United States Patent [19]

Melcher et al.

[11] Patent Number: 4,873,489
[45] Date of Patent: Oct. 10, 1989

[54] METHOD AND APPARATUS FOR MEASUREMENT OF CHARGE ENTRAINED IN FLUIDS

[75] Inventors: James R. Melcher, Lexington; Alfred J. Morin, II, Cambridge; Markus Zahn, Lexington, all of Mass.

[73] Assignee: Massachusetts Institute of Technology, Cambridge, Mass.

[21] Appl. No.: 163,384

[22] Filed: Mar. 2, 1988

[51] Int. Cl.⁴ ............................................ G01R 31/12
[52] U.S. Cl. ................................... 324/453; 324/547; 324/553
[58] Field of Search ............... 324/453, 457, 547, 553, 324/454; 73/64, 864.62; 361/35

[56] References Cited

U.S. PATENT DOCUMENTS

| | | |
|---|---|---|
| 2,756,388 | 7/1956 | McLean . |
| 3,040,250 | 6/1962 | Fuchs ................... 324/553 |
| 3,368,144 | 2/1968 | Gerdes . |
| 3,405,722 | 10/1968 | Carruthers et al. ............... 324/453 |
| 3,453,538 | 7/1969 | Wright et al. .................... 324/72 |
| 3,585,861 | 6/1971 | Keng . |
| 4,194,148 | 3/1980 | Ohkubo . |
| 4,249,131 | 2/1981 | Owen ................................ 324/457 |
| 4,309,661 | 1/1982 | Kamoto ............................ 324/453 |
| 4,449,101 | 5/1984 | Canzoneri ........................ 324/453 |
| 4,463,316 | 7/1984 | Messens et al. .................. 324/453 |

FOREIGN PATENT DOCUMENTS

496487 12/1975 U.S.S.R. .............................. 324/454

OTHER PUBLICATIONS

Markus Zahn, *Electromagnetic Field Theory: a Problem Solving Approach*, (N.Y.: John Wiley & Sons, 1979), pp. 53-54.

*Electrostatics in the Petroleum Industry*, A Royal Dutch/Shell and Development Report, Eds. A. Klinkenberg and L. J. van der Minne (Amsterdam: Elsevier Publishing Company, 1958), pp. 49-51, 119-123, 132, 166-168.

T. V. Oommen et al., "Electrostatic Charging Tendency of Transformer Oils," IEEE, 1984, pp. 1-9.

T. Tanaka et al., "Model Approach to the Static Electrification Phenomena Induced by the Flow of Oil in Large Power Transformers," IEEE, 1980, pp. 1097-1106.

H. Okubo et al., "Charging Tendency Measurement of Transformer Oil," IEEE, 1979, pp. 1-8.

*Primary Examiner*—Reinhard J. Eisenzopf
*Assistant Examiner*—Maura K. Regan
*Attorney, Agent, or Firm*—Hamilton, Brook, Smith & Reynolds

[57] ABSTRACT

The density of charge entrained in fluids such as oils in transformer systems, capacitors, cables, pumps and fuel transfer systems is measured by introducing the oil into a conductive container which expands in volume to receive the fluid without expelling any fluid. The container is shielded by a grounded conductor which prevents inducement of charge on the container by external sources. By measuring the current between the conducting expandable container and the surrounding shield and accounting for the effects of the charge induced on the outer wall of the container by its own induced voltage, the net charge entrained in the fluid as it is brought into the container is deduced. Extraneous effects of conduction and electrokinetic currents are automatically excluded from the measurement. The oil is then automatically returned to the transformer system by the contraction of the conductive container so that the measurement can be repeated without accumulating an inventory of fluid.

51 Claims, 6 Drawing Sheets

METHOD AND APPARATUS FOR MEASUREMENT OF CHARGE ENTRAINED IN FLUIDS

BACKGROUND OF THE INVENTION

Large power transformers are generally cooled by oil which passes through the transformers to collect heat and then through a heat exchanger to release the heat. Catastrophic failures of large power transformers have been traced to electrification of the oil. An electric field is generated by the convection of oil through the windings, with the oil playing the role of a Van de Graaff generator belt. There is a major need for a device that can be used to provide an unambiguous measurement of the net charge entrained in the oil.

Prior to the present invention, attempts to provide absolute measurement of the charge entrained in the oil or other fluid have been unsuccessful. The attempts include the direct pickup of charge by ground as well as capacitive pickups. In the first type of sensor, where the measured quantity is a conduction current, even if measures are taken to control the fields induced by the net charge so that the measured current might be related to the absolute charge density entrained in the liquid, one can never be certain whether the net charge is causing the detected current or whether the detected current is in part or even wholly due to charge removed from the electrode by the flow. Techniques that make use of a large settling chamber, where there is presumably a sufficient residence time of the fluid for charge relaxation to reach completion, suffer from requiring an inconveniently large inventory of liquid and always leave open the question of whether or not the fluid leaving the settling chamber does so without carrying charge. This latter charge, which would make a misleading contribution to the measured current, could either result because the charge relaxation process had not reached completion or because of entrainment of charge in the chamber by the very electrification process to which the instrument is to be applied. In the second type of instrument, there is an inherent difficulty in distinguishing between capacitive and conduction currents. Any device actually in contact with the fluid will be subject to conduction and electrification currents. If the device is separated from the fluid by an insulating layer, there will always be the question of whether or not part of the charge being measured is due to the insulating layer and therefore artifactual.

DISCLOSURE OF THE INVENTION

In accordance with the present invention, fluid, such as hydrocarbon fuel or the oil from a power transformer, is drawn into an electrically conductive, mechanically closed container, and an electrical signal developed between the container and the shield by net charge carried by the fluid is detected. Once within the container, current from the container may be detected as an absolute measure of the net charge carried by the sampled fluid, regardless of whether that charge is subsequently conducted from the fluid to the container or, in the case of highly insulating liquids such as recently processed transformer oil, remains entrained in the sample of fluid. Further, because any charge entrained in the fluid by the sampling process is compensated by a net charge of the opposite polarity on the walls of the sampling container, the detected current is not influenced by electrokinetic effects so long as such effects in transfer of the fluid from a sampled volume to the conductive container are minimized. The fluid is also introduced into the container in a time which is short compared to the charge relaxation time in the fluid. After detection of the charge, provision is made for expelling the fluid from the container. Thus, repeated measurements can be made, with only a small amount of fluid ever removed from or added to the system being monitored at any time, but with no net fluid removed or added over the measurement cycle. A shield around the sampling container prevents the induction of charge on the container other than by the charge carrying fluid.

To maximize shielding, the conducting conduit of a probe used to sample the charged fluid is itself insulated from but shielded by the same shield as used to shield the sampling container. To virtually eliminate any charge being induced on the metal walls of the sampling volume, including the walls of the sampling conduit, by fields due to charges outside the sampling volume, the entrance of the sampling conduit can be recessed several sampling tube diameters inside the shield. Thus, the sampling conduit can be comprised of a conductive probe that carries fluid to a main volume, that probe itself being shielded with the main volume so that the two together form the shielded container. the shield for that part of the conducting probe that extends into the fluid also prevents currents of electrokinetic and chemical origin from making a contribution to the measured current.

The fluid may be drawn into the conductive container by means of a positive displacement device having a conductive surface which is driven from outside of the shield by an insulated coupling. A preferred positive displacement device is a metal bellows. A spring acting against the bellows may oppose the head pressure of the fluid. Alternatively, the fluid may be forced into the container by the positive pressure of the main volume and subsequently be expelled by pressurized gas. The fluid may be taken into the container and expelled through respective one-way, check valves. These valves can also be electronically actuated for improved performance. In this way the fluid can be expelled in a region well removed from that from which it is sampled. If the sampling region is one where the fluid is in motion and hence where an expelled sample will be carried away, a single conduit can be used for both sampling and expulsion with no check valves. In either case, there can be a controlled period between the expulsion of the fluid and the taking of the next sample.

The capacitance between the container and the shield is best maintained constant. To that end, an electrode may be mechanically coupled to the container; the electrode is electrically insulated from the container and electrically coupled to the shield. Alternatively, the container may be mechanically and electrically coupled to a guard conductor which surrounds the container. For further ease of measurement, the current between the container and shield is detected only after a steady flow of fluid into the container is obtained.

BRIEF DESCRIPTION OF THE DRAWINGS

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

FIG. 5b illustrates the current measured by a low impedance electrometer in its current mode with the introduction and expulsion of charged liquid as in FIG. 5a;

DESCRIPTION OF PREFERRED EMBODIMENTS

Figure 1:
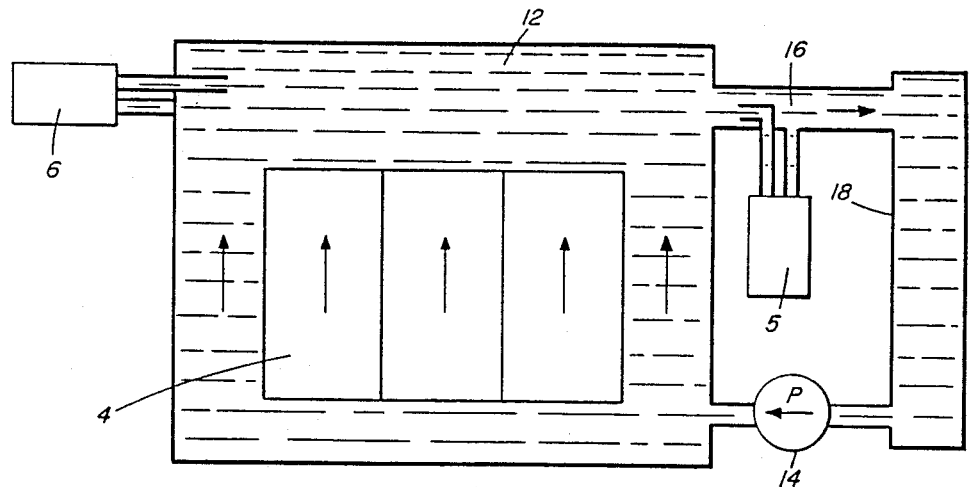
FIG. 1 is a schematic illustration of a power transformer system having two charge measuring devices embodying the present invention.

FIG. 1 illustrates a power transformer unit 12. Oil may be forced by a pump 14 into the transformer 4 for cooling. Alternatively, the cooling may be accomplished through natural convection. In either case, most of the oil passes through a conduit 16 to a heat exchanger 18 and is recycled through the transformer. In accordance with the present invention, a charge measurement device 5 is coupled to the conduit 16. So long as it is consistent with the insulation requirements of the transformer, the device may be coupled anywhere else in the system, such as at 6 adjacent to the header region of the transformer.

Figure 2:
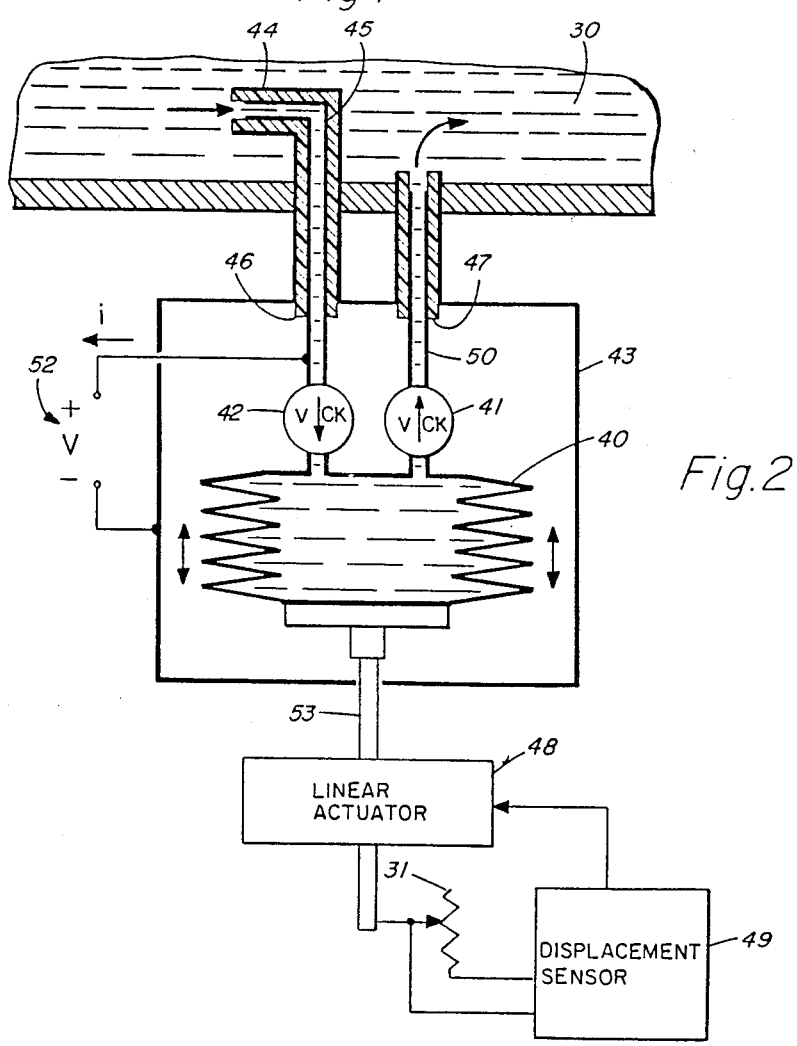
FIG. 2 is an electrical and mechanical schematic of the absolute charge sensing instruments of FIG. 1.

A schematic of the detector is illustrated in FIG. 2. The fluid 30, oil in the case of the transformer, is drawn into an electrically conductive container. That container includes the inner probe needle 45, an inlet check valve 42, a bellows assembly 40, an outlet check valve 41 and an outlet inner conduit 50. The inner conducting conduits of the probe, of the inlet and outlet valves, of the bellows and of the outlet conduit are surrounded by a grounded shield 43,44. The inner conducting needle probe 45 and surrounding shield 44 are separated by insulating material 46 and the outlet conducting conduit is separated from the shield by insulating material 47. The bellows is separated from the shield by an insulating fluid such as air. The lower closed end of the bellows is driven by a linear actuator 48 through an electrically insulating shaft 53 whose position is monitored by potentiometer 31 with a displacement sensor 49. When the shaft is pulled down, the bellows is expanded to draw oil through the probe 45 and check valve 42. Charge is detected by means of a wire attached to the inner conductor and a wire connected to the shield to form the terminal pair 52. The liquid is then expelled through a second check valve 41 and through the shielded conduit 50.

Alternatively, if the liquid to be sampled is in motion so that the sample can be returned through the probe, the outlet tube and check valve are omitted from the system, as is the inlet check valve. In this mode of operation, the shaft is pulled down, the bellows is expanded to draw oil through the probe 45 directly into the bellows. After the charge is detected, the liquid is in this mode expelled through conduit 45.

Figure 3:
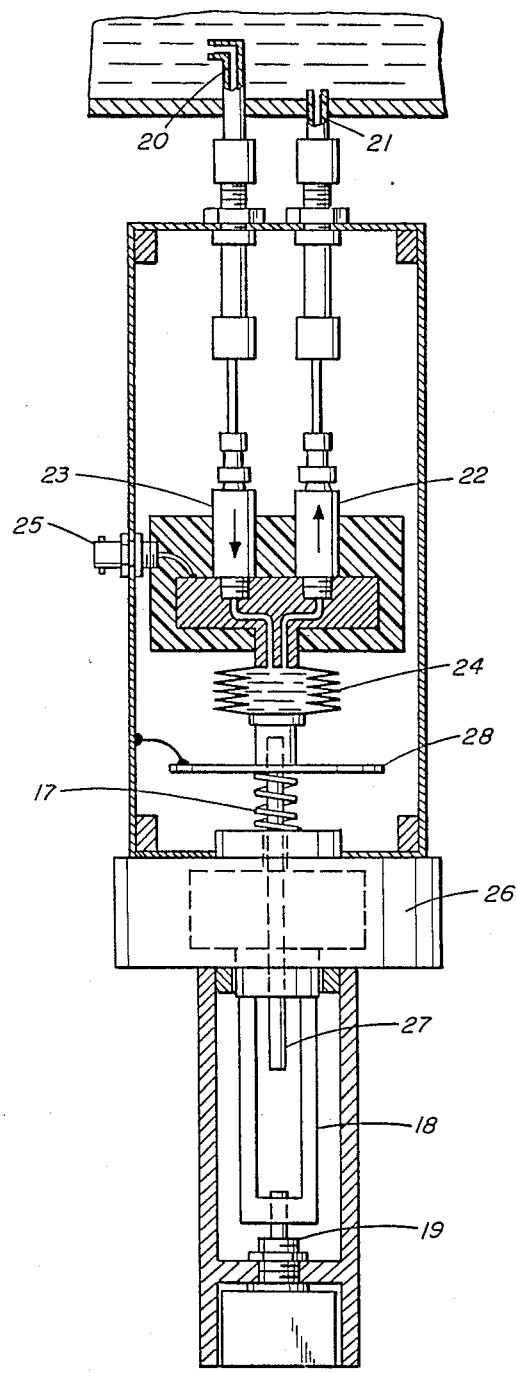
FIG. 3 is a detailed illustration of one embodiment of the invention.

One embodiment of the sensor illustrated schematically by FIG. 2 is shown in FIG. 3. The inlet probe is 20 while the outlet conduit is 21. The inlet check valve is 23 while the outlet check valve is 22. These are mounted on an insulated metal base that is mechanically and electrically contiguous with the bellows 24 and is electrically connected to the center conductor of the coaxial output connector 25. The insulating driving shaft 27 connects the bellows to the linear actuator 26 through a motion coupler 18 and position sensing potentiometer 19. Spring 17 compensates for the hydrostatic head of fluid supported by the conductive container.

In the voltage mode of operation, the capacitance between the conducting inner conductor and the surrounding shield figures in relating the output voltage to the absolute charge density. The conducting plate 28 is mechanically connected to the movable end of the bellows and electrically grounded. Thus, as an extension of the shield that maintains its position relative to the movable end of the bellows, it minimizes the change, with bellows expansion, in the capacitance between the inner conductor and the surrounding shield.

From experiments made famous by Faraday, it is known that a charged body introduced into the perfectly insulating volume surrounded by a conductive container will induce an opposite charge on the interior wall of the container. Thus, without actually being transported to the wall, the net charge carried into the conductive container would be equal to but of opposite polarity to that on the inner wall. Because the rate of accumulation of the charge so induced on the inner wall of the container comprises an electrical current that can be measured externally, it is then possible to measure this net charge by means of an external circuit having a sufficiently low impedance that the potential of the container would remain essentially zero relative to that of the surrounding shield.

In actuality, the fluid is not a perfect insulator. Thus, in addition to the image charge induced on the wall, there are two other currents that can exist at each point on the wall. One is a conduction current, associated with the electric field caused by the net charge. The other is a current due to the very electrokinetic process possibly responsible for the charge to be measured. As the fluid passes over any part of the surface, there is likely to be a current density of electrokinetic origin. Thus, at a point on the surface where net charge is carried away by the moving liquid, there is likely to be a contribution to the net current into the conducting wall. In fact, it is this current that renders the signals provided by other proposed instruments of dubious significance.

Figure 4:
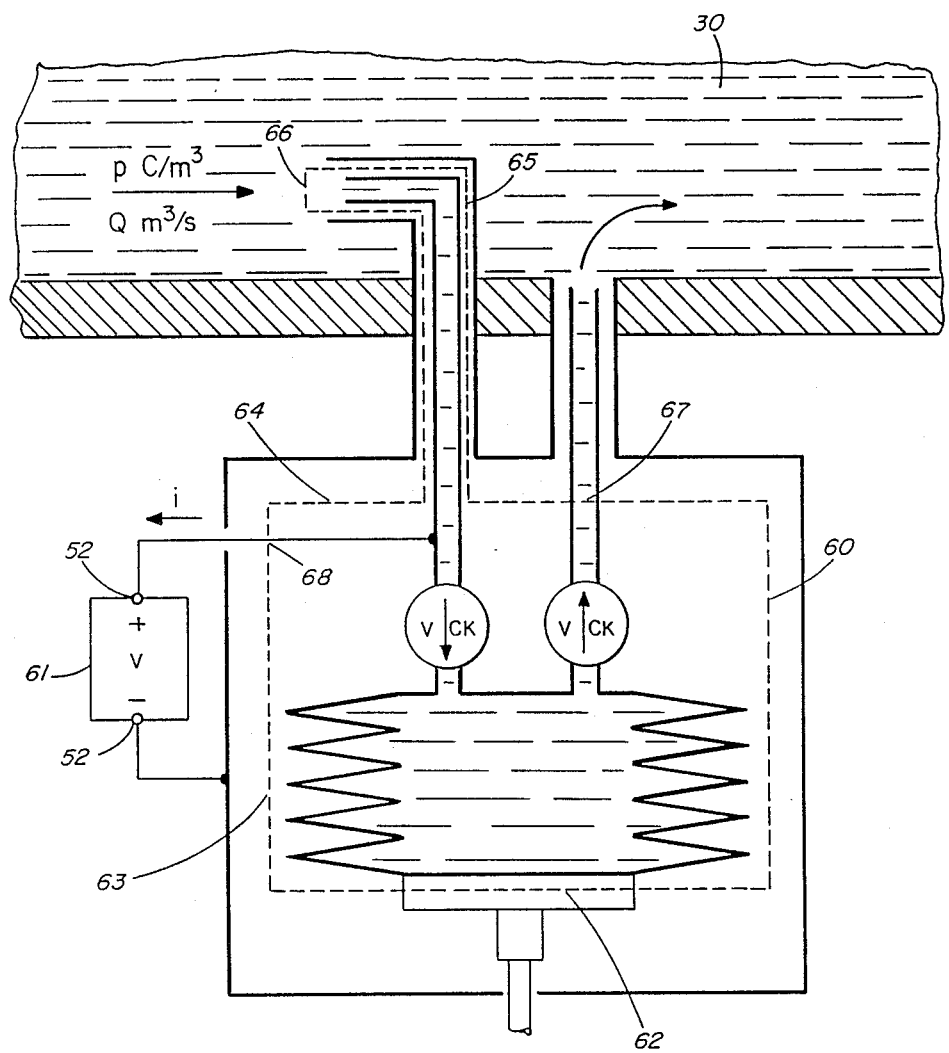
FIG. 4 illustrates the surface enclosing the volume within which charge conservation is exploited.

The surface 60 shown in FIG. 4 can be used to see how the disclosed invention avoids the errors caused by possible conduction and electrokinetic currents. This surface completely encloses the metal container. The surface 60 passes through the insulating mechanical coupling to the bellows at 62, between the bellows and the grounded shield on the sides and top, 63 and 64, and through the insulating annular region between the inner conductor and outer shield of the inlet at 65, and is finally completely closed through the sampled liquid at the inlet at 66 and outlet at 67. The electrical terminals 52 between the conductive container and shield are connected by an electrometer 61 which can measure terminal voltage or current.

The surface 60 is conceived so that, except where it passes through the fluid as it enters the probe duct at 66 and where the fluid is returned during the expulsion phase but is stagnant during the sampling phase at 67 and except where it passes through the wire connecting the inner container to the output terminal at 68, the surface is in regions such as 62, 63 and 65 where the insulation can be made essentially ideal. Thus, the law of conservation of charge for the volume enclosed by the surface 60, can be written in terms of the convection current, the product of the volume rate of flow, Q, and the charge density that is to be measured, $\rho$, the current i available at the output terminals and the charge induced on the highly conducting exterior surface of the inner container. Charge conservation requires that the transfer of charge into the container by the flow of liquid must equal the current i through the wire plus the rate of change with respect to time of the charge, q, on the exterior surface of the inner container. Thus, $$\rho Q = i + \frac{dq}{dt} \quad (1)$$

Note that the possible error current at 67 is made negligible by insuring that the fluid is stagnant there and can carry no charge by convection and that any conduction current that might be due to net charge in the fluid is essentially in the radial direction within the outlet conduit and therefore not capable of making a contribution to (1). Of course, when operated in the mode where the inlet conduit is also used to expel the fluid, 67 does not exist and the question of error currents coming from such a region is moot.

Because the outer surface of the inner container and the inner surface of the surrounding shield are highly conducting, there is a well established relation between the charge on the outside of the inner container and the voltage, v, between that container and the surrounding shield. With C defined as the capacitance of the inner container relative to the shield $$q = Cv \quad (2)$$

For convenience the apparatus should be designed so that C remains essentially constant during the expansion of the bellows. The embodiment exemplified by FIG. 3 shows a part of the grounded shield 28 that is attached to the bellows so that it retains an essentially constant position relative to the nearest end of the bellows.

In order to detect the voltage or current at the output terminal, an electrometer is attached to the terminals as in FIG. 4. This device can be represented by a resistor R attached to the terminals, thus electrically connecting the inner container and the grounded shield. As charge is discharged from the outer surface of the container to ground, it will be seen as a current i which causes a voltage v across the resistor.

Figure 5A:
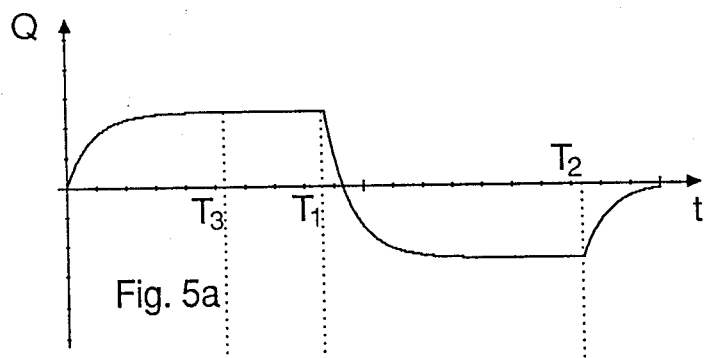
FIG. 5a is the volume rate of flow of the liquid into and out of the sampling volume.

If the oil is drawn into the container at a constant rate, the flow rate Q is V/T where V is the difference between final and initial volumes of the fluid within the inner conducting region and T is the time during which oil is drawn into the container. Because the instantaneous bellows volume is to some degree responsive to pressure drop sustained by passage of the liquid through the inlet duct, even if the linear actuator is designed to provide a constant displacement of the bellows movable end, the time-dependence of the volume rate of flow, Q, is as shown in FIG. 5a. By the time $T_3$, Q is essentially constant until the expansion is terminated when the time is $T_1$. For the case shown, the fluid is then returned through the outlet duct; or with the apparatus configured without an outlet duct and the check valves, the fluid is returned through the same duct used for drawing the fluid into the bellows. In some applications, it may be desirable to return the fluid during a later time interval.

With the detection electrometer attached to the terminals represented by a resistance, R, $v = iR$ and (1) and (2) become $$\rho Q = \frac{v}{R} + \frac{Cdv}{dt} \quad (3)$$

The same information is provided by using these relations to relate the sampled charge density to the current rather than the voltage.

$$\rho Q = i + RC\frac{di}{dt} \quad (4)$$

Although these relations can be used to deduce $\rho Q$ from the measurement of either of the electrical signals v or i, regardless of the value of RC relative to the sampling time, $T_1$, there are two limiting modes of measurement.

It can be seen from (4) that, if the time RC is very small compared to the sampling time, $T_1$, the second term on the right side of the equation is negligible so that $$\rho = \frac{i}{Q} \quad (5)$$

Figure 5B:
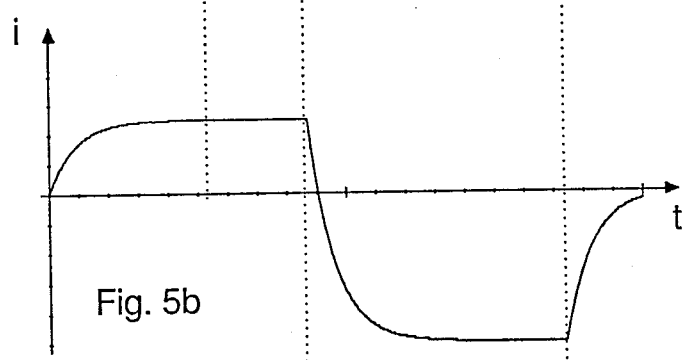

Thus, with the current measured using an electrometer having a sufficiently low impedance that $RC \ll T_1$, the current has the time dependence illustrated by FIG. 5b. An absolute measurement of the charge density is made by simply dividing the current measured between $T_3$ and $T_1$ by the volume rate of flow. Because the volume rate of flow is simply determined during this period of the bellows expansion from the velocity of the end of the bellows attached to the linear actuator, in practice it is convenient to record i during the period between $T_3$ and $T_1$ in FIG. 5a. Improved accuracy is provided by averaging measurements made throughout this time interval.

Note that the area under the curve of FIG. 5b is not the same during the expulsion interval as during the sampling period. This illustrates the fact that, as the fluid is both drawn into the bellows and then expelled, electrokinetic effects indeed result in an entrained charge. Because the measurement is made during the interval $T_3$ to $T_1$, the expulsion of this charge has no influence on the measurement. But, more important, during the measurement interval there is no influence of this entrained charge because what charge is entrained is balanced by the counter charge remaining on the inner container wall. When the fluid is returned, it may well be with a greater charge density than that sampled, because of this charging due to the relative motion between the fluid and the bellows and conduit comprising the inner conductor.

From (3) it can also be seen that, if the resistance of the electrometer is so large that the time RC is very large compared to $T_1$, the first term to the right of the equation becomes insignificant. In that case, the charge density can be determined from $$\rho = \frac{C}{Q} \frac{dv}{dt} \quad (6)$$

Figure 5C:
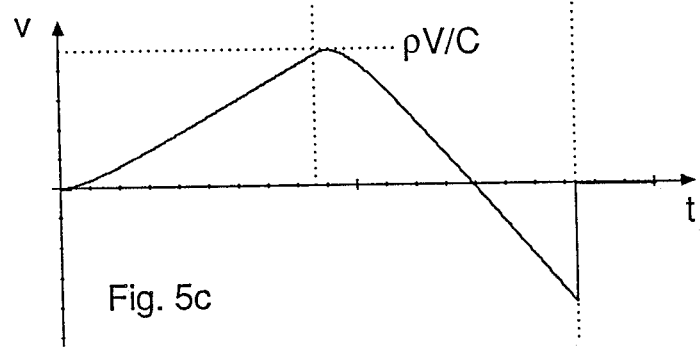
FIG. 5c illustrates the voltage measured by a high impedance electrometer in its voltage mode with the same introduction and expulsion of charged liquid.

Thus, in this second limiting measurement mode, the desired charge density can be deduced from differentiation of the voltage measured by a high impedance electrometer. Once again the volume rate of flow must be deduced from the rate of bellows expansion. In addition, however, the capacitance C of the inner container relative to its shield must be measured. However, by designing the system so that C is essentially independent of the bellows expansion, this must only be done once. Typically, the voltage in this high impedance measurement mode has the time dependence shown in FIG. 5c. Because the charge density of the expelled fluid is in general different from that sampled, the voltage does not return to zero after one cycle. Thus the voltage must be reset before each measurement cycle when the instrument is used in this high impedance mode.

The current mode is preferred because measurements deduced in the voltage mode depend on C, which is altered if the sampling probe is changed, because even the small change in C inherent to a well designed instrument complicates the deduction of the charge density and because the terminals must be shorted before the next cycle. The current mode is an idealization. As a practical matter, the voltage will be finite but small and the capacitance will have some small effect. It is therefore desirable to keep the capacitance constant during the sampling period even when operation is essentially in the current mode.

Figure 6:
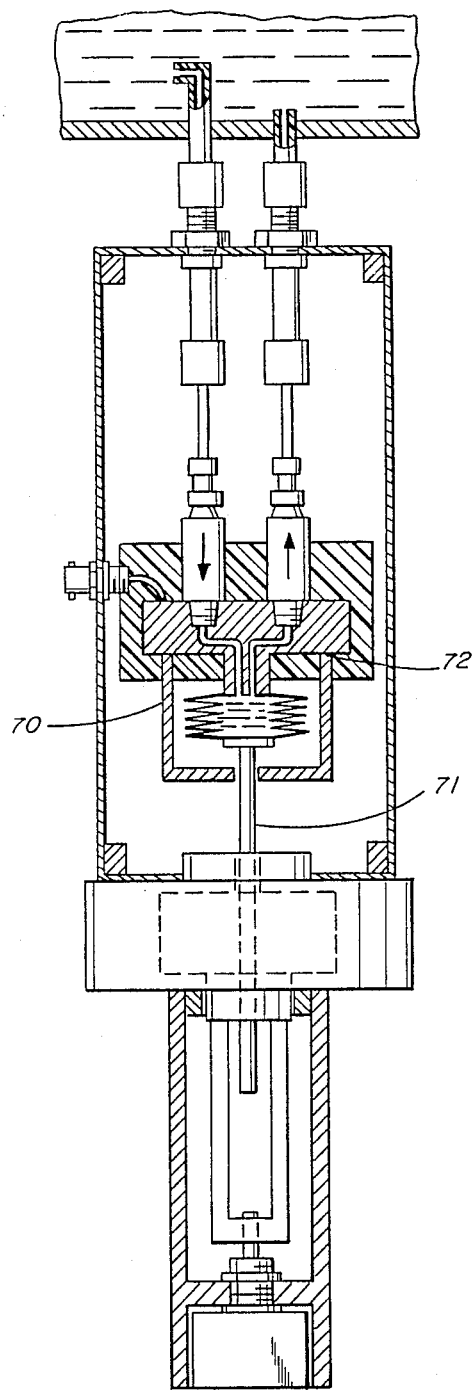
FIG. 6 illustrates an alternative embodiment in which a fixed conductor is electrically connected to the bellows assembly so as to make the capacitance C remain constant while the bellows changes volume.

An alternative to the movable extension of the shield 28 for minimizing variations in the capacitance C with expansion of the bellows is illustrated by FIG. 6. The capacitance variation with expansion of the volume of the conductive container is minimized by a fixed mechanical and electrical extension 70 of the conductive container which surrounds the part of the conductive container that changes volume during the sample period. This guard conductor extension 70 is attached to the conductive container at 72 in the illustration. To avoid variations in the capacitance due to changes in the position of the shaft 71, the shaft is made from an insulating material.

The shielding of the inner container by the grounded shield 43 prevents any inducement of charge on the inner container from an external source. Thus, the only charge which is measured is that which is introduced into the container by the oil. To assure the accuracy of the measurement, the entrance of the sampling tube should be designed with the inner conductor recessed sufficiently to prevent the induction of charge on its surface by external fields. Thus, the recession length should be more than a conduit diameter. However, it should also not be recessed so far that there is an appreciable entrainment of charge from the surface of the insulator that forms the conduit between the tip of the probe and the inner conducting sampling conduit 69. For practical purposes, this is accomplished in most fluids and with most insulating conduit materials by making the recession length no more than a few diameters and making the flow in the sampling probe laminar. The transit time of the fluid over the recession length should be short compared to the electrical relaxation time $\epsilon/\sigma$, where $\epsilon$ is the permittivity and $\sigma$ is the conductivity of the fluid. It is also very important that the measurement be completed before charged liquid is returned to the sampled volume 30. Otherwise, charge which is entrained within the oil or released from the oil to the container would cause an ambiguous reading. However, by returning the oil after a measurement, the device can be operated repetitively with no net accumulation of oil.

The volume V of fluid that must be collected is determined by the impedance of the device connected to the output terminals. In the current mode, it is determined by the lowest current level that can be measured and by the requirement that the RC time constant of the detector be short compared to $T_1$. The approach can be used with an extremely small volume of liquid in the current mode where the capacitance C is also very small. Thus, the entire system may be formed on a microfabricated chip.

Figure 7:
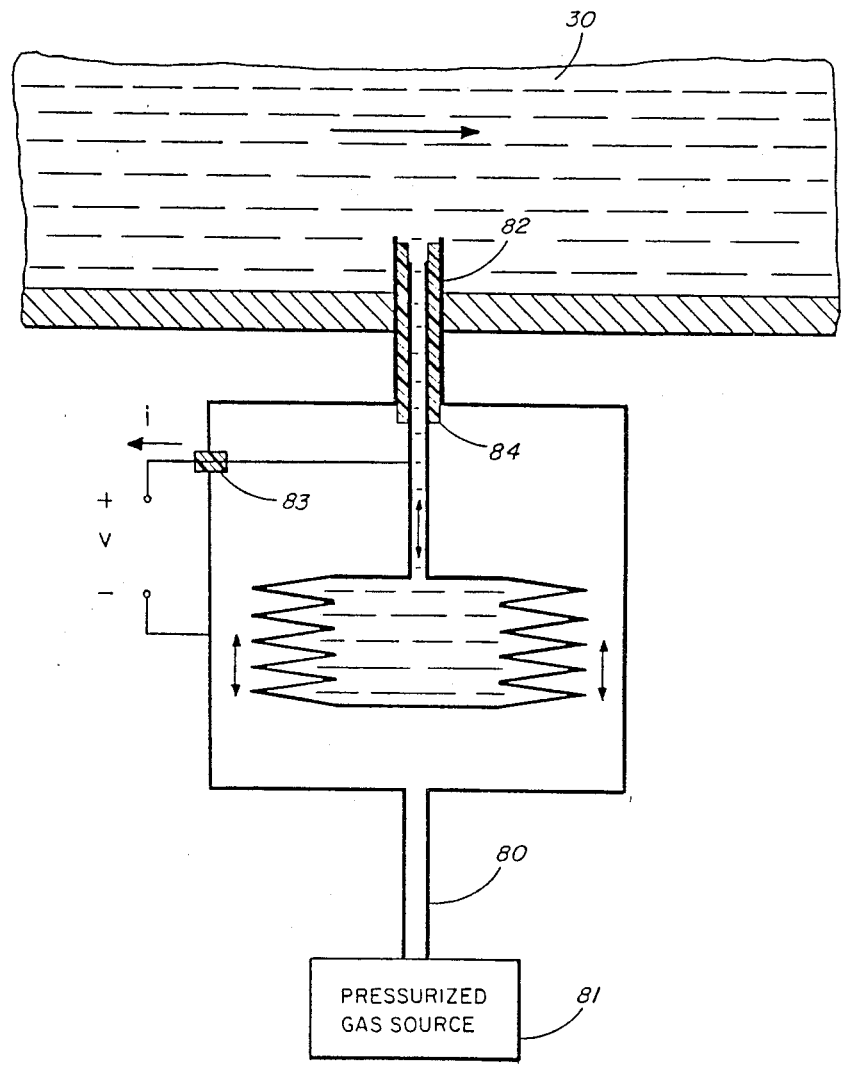
FIG. 7 illustrates yet another embodiment in which a single electrically conducting conduit is used to both intake and expel the sampled fluid and in which the fluid intake is driven by the positive pressure of the sampled fluid and expelled by a modulated external pressure source.

As an alternative to the bellows, the positive displacement device may be a piston which is electrically conductive and coupled to the remainder of the container. Alternatively, FIG. 7 shows a system in which the positive pressure of the oil in the fluid 30 is used to drive the oil into the container and the oil is thereafter expelled by pressurized gas from a modulated source 81 through gas conduit 80. FIG. 7 also shows a single electrically conducting conduit 82 used to both intake and expel the sampled fluid. The fluid flow can carry away the sampled fluid and bring in fresh fluid before the next measurement cycle. Insulators 83 and 84 seal the volume within the shield. As in other embodiments, the fluid may be transformer oil, hjydrocarbon fuel or other fluid able to entrain charge.

While this invention has been particularly shown and described with references to preferred embodiments thereof, it will be understood by those skilled in the art that various changes in form and details may be made therein without departing from the spirit and scope of the invention as defined by the appended claims.

We claim:

1. Apparatus for measuring the net charge entrained in a fluid comprising:
   an electrically conductive container;
   an electrically conductive shield surrounding and insulated from the container;
   means for introducing fluid into the container and thereafter expelling the fluid from the container; and
   a detector for detecting, before any introduced fluid is expelled, an electrical signal developed between the container and the shield when the container is filled with fluid.

2. Apparatus as claimed in claim 1 wherein the container comprises a shielded, conductive probe through which the fluid is received.

3. Apparatus as claimed in claim2 wherein the probe is recessed inside the conducting shield by a distance that is on the order of the width of an aperture in the shield through which the fluid is received.

4. Apparatus as claimed in claim 1 wherein the container is filled through a port which is recessed inside the conducting shield by a distance that is on the order of the width of an aperture in the shield through which the fluid is received.

5. Apparatus as claimed in claim 1 wherein the means for introducing fluid into the container and expelling the fluid comprises a positive displacement element.

6. Apparatus as claimed in claim 5 wherein the positive displacement element is a bellows.

7. Apparatus as claimed in claim 1 wherein the means for introducing fluid into the container and expelling the fluid includes a source of pressurized gas.

8. Apparatus as claimed in claim 1 wherein the means for introducing fluid into the container and expelling the liquid comprises one-way valves in separate conduits.

9. Apparatus as claimed in claim 1 wherein the means for introducing fluid into the container and expelling the oil comprises a common port.

10. Apparatus as claimed in claim 1 further comprising means for minimizing change in capacitance between the container and shield as fluid is introduced into the container.

11. Apparatus as claimed in claim 10 wherein the means for minimizing the change in capacitance comprises an electrode coupled to move with but electrically insulated from the conductive container and which is electrically connected to the shield.

12. Apparatus as claimed in claim 10 wherein the means for minimizing change in capacitance comprises a guard conductor surrounding a part of the conductive container that moves as fluid is introduced into the container, the guard conductor being electrically connected to the container.

13. Apparatus as claimed in claim 1 wherein the conducting container and shield are microfabricated.

14. Apparatus as claimed in claim 1 wherein means for introducing fluid into the container and expelling the fluid comprises a positive displacement element and a spring for countering a pressure head of the fluid against the positive displacement element.

15. Apparatus as claimed in claim 1 wherein the detector detects the electrical signal only during a time in which a steady flow of fluid is introduced into the container.

16. Apparatus as claimed in claim 1 wherein the electrical signal is a voltage between the container and the shield.

17. Apparatus as claimed in claim 1 wherein the electrical signal is a current relative to the container.

18. Apparatus for measuring the net charge entrained in a fluid in a sampled volume comprising:
an electrically conductive container, the volume of which can accommodate the sampled fluid while retaining electrical continuity and while not at the same time expelling the fluid;
an electrically conductive shield surrounding and insulated from the conductive container;
means for introducing fluid into the container in a time that is short compared to the charge relaxation time in the fluid and without significant entrainment of charge with flow of the fluid from the sampled volume to the container and for thereafter expelling the fluid from the container; and
a detector for detecting, befor any introduced fluid is expelled, an electrical signal developed between the container and the shield when fluid is introduced into the container.

19. Apparatus as claimed in claim 18 wherein the container comprises a shielded, conductive probe through which the fluid is received.

20. Apparatus as claimed in claim 19 wherein the probe is recessed inside the conducting shield by a distance that is on the order of the width of an aperture in the shield through which the fluid is received.

21. Apparatus as claimed in claim 18 wherein the container is filled through a port which is recessed inside the conducting shield by a distance that is on the order of the width of an aperture in the shield through which the fluid is received.

22. Apparatus as claimed in claim 18 wherein the means for introducing fluid into the container and expelling the fluid comprises a bellows.

23. Apparatus as claimed in claim 18 wherein the means for introducing fluid into the container and expelling the fluid includes a source of pressurized gas.

24. Apparatus as claimed in claim 18 further comprising a guard conductor surrounding a part of the conductive container that moves as fluid is introduced into the container, the guard conductor being electrically connected to the container to minimize change in capacitance between the container and shield.

25. Apparatus as claimed in claim 18 wherein the electrical signal is a voltage between the container and the shield.

26. Apparatus as claimed in claim 18 wherein the electrical signal is a current relative to the container.

27. A method of measuring the net charge entrained in a fluid comprising:
introducing the fluid into an electrically conductive and shielded container; and
measuring an electrical signal developed between the container and the shield when the fluid is introduced into the container before release of any of the fluid from the container.

28. A method as claimed in claim 27 wherein the electrical signal is a voltage between the container and the shield.

29. A method as claimed in claim 27 wherein the electrical signal is a current relative to the container.

30. A method of measuring the net charge entrained in a fluid in sampled volume comprising:
introducing the fluid into an electrically conductive and shielded container in a time that is short compared to the charge relaxation time in the fluid and without significant entrainment of charge with flow of the fluid from the sampled volume to the container; and
measuring an electrical signal developed between the container and the shield before release of any of the fluid from the container.

31. A method as claimed in claim 30 wherein the container comprises a shielded, conductive probe through which the fluid is introduced to the container.

32. A method as claimed in claim 31 wherein the probe is recessed inside the conducting shield by a distance that is on the order of the width of an aperture in the shield through which the fluid is received.

33. A method as claimed in claim 30 wherein the container is filled through a port which is recessed inside the conducting shield by a distance that is on the order of the width of an aperture in the shield through which the fluid is received.

34. A method as claimed in claim 30 wherein the container comprises a bellows.

35. A method as claimed in claim 30 further comprising the step of expelling the fluid from the container by means of pressurized gas.

36. A method as claimed in claim 30 wherein the electrical signal is a voltage between the container and the shield.

37. A method as claimed in claim 30 wherein the electrical signal is a current relative to the container.

38. A method of measuring the charge entrained in oil in a transformer system comprising:
introducing the oil into an electrically conductive and shielded container; and
measuring an electrical signal developed between the container and the shield before release of any of the oil from the container.

39. A method as claimed in claim 38 wherein the fluid is introduced into the container through a shielded conductive probe.

40. A method of measuring the charge entrained in fuel comprising:
introducing the fuel into an electrically conductive and shielded container; and
measuring an electrical signal developed between the container and the shield before release of any of the fuel from the container.

41. A method as claimed in claim 40 wherein the fluid is introduced into the container through a shielded conductive probe.

42. Apparatus for measuring the net charge entrained in a fluid comprising:
an electrically conductive container comprising a shielded, conductive probe through which the fluid is received;
an electrically conductive shield surrounding and insulated from the container;
means for introducing fluid into the container and thereafter expelling the fluid from the container; and
a detector for detecting an electrical signal developed between the container and the shield when the container is filled with fluid.

43. Apparatus as claimed in claim 42 wherein the probe is recessed inside the conducting shield by a distance that is on the order of the width of an aperture in the shield through which the fluid is received.

44. Apparatus for measuring the net charge entrained in a fluid comprising:
an electrically conductive container;
an electrically conductive shield surrounding and insulated from the container;
a positive displacement element for introducing fluid into the container and thereafter expelling the fluid from the container; and
a detector for detecting an electrical signal developed between the container and the shield when the container is filled with fluid.

45. Apparatus as claimed in claim 44 wherein the positive displacement element is a bellows.

46. Apparatus for measuring the net charge entrained in fluid comprising:
an electrically conductive container;
an electrically conductive shield surrounding and insulated from the container;
means comprising one-way valves in separate conduits for introducing fluid into the container and thereafter expelling the fluid from the container; and
a detector for detecting and electrical signal developed between the container and the shield when the container is filled with fluid.

47. Apparatus for measuring the net charge entrained in a fluid comprising:
an electrically conductive container;
an electrically conductive shield surrounding and insulated from the container;
means for introducing fluid into the container and thereafter expelling the fluid from the container through a common port; and
a detector for detecting an electrical signal developed between the container and the shield when the container is filled with fluid.

48. Apparatus for measuring the net charge entrained in a fluid comprising:
an electrically conductive container;
an electrically conductive shield surrounding and insulated from the container;
means for introducing fluid into the container and thereafter expelling the fluid from the container;
a detector for detecting an electrical signal developed between the container and the shield when the container is filled with fluid; and
means for minimizing change in capacitance between the container and shield as fluid is introduced into the container.

49. Apparatus as claimed in claim 48 wherein the means for minimizing the change in capacitance comprises an electrode coupled to move with but electrically insulated from the conductive container and which is electrically connected to the shield.

50. Apparatus as claimed in claim 48 wherein the means for minimizing change in capacitance comprises a guard conductor surrounding a part of the conductive container that moves as fluid is introduced into the container, the guard conductor being electrically connected to the container.

51. Apparatus for measuring the net charge entrained in a fluid comprising:
an electrically conductive container;
an electrically conductive shield surrounding and insulated from the container;
means for introducing fluid into the container and thereafter expelling the fluid from the container, the means for introducing fluid into the container and expelling the fluid comprising a positive displacement element and a spring for countering a pressure head of the fluid against the positive displacement element; and
a detector for detecting an electrical signal developed between the container and the shield when the container is filled with fluid.

* * * * *